(12) United States Patent
Haaja et al.

(10) Patent No.: US 8,632,544 B2
(45) Date of Patent: Jan. 21, 2014

(54) INTERNAL OSTEODISTRACTION DEVICE

(75) Inventors: Juha Haaja, Espoo (FI); Antti Ritvanen, Espoo (FI); Markus Turunen, Nastola (FI); Harri Hallila, Helsinki (FI)

(73) Assignee: Synoste Oy, Helsinki (FI)

( * ) Notice: Subject to any disclaimer, the term of this patent is extended or adjusted under 35 U.S.C. 154(b) by 431 days.

(21) Appl. No.: 12/736,149

(22) PCT Filed: Mar. 19, 2009

(86) PCT No.: PCT/FI2009/050209
§ 371 (c)(1),
(2), (4) Date: Sep. 15, 2010

(87) PCT Pub. No.: WO2009/115645
PCT Pub. Date: Sep. 24, 2009

(65) Prior Publication Data
US 2011/0004246 A1    Jan. 6, 2011

(30) Foreign Application Priority Data

Mar. 19, 2008 (FI) .................................. 20085238

(51) Int. Cl.
*A61B 17/72* (2006.01)
(52) U.S. Cl.
USPC ............................................... 606/63
(58) Field of Classification Search
USPC ............................. 606/62–68, 326
See application file for complete search history.

(56) References Cited

U.S. PATENT DOCUMENTS

| | | | | |
|---|---|---|---|---|
| 4,834,225 | A | * | 5/1989 | Klopfenstein et al. ........ 192/223 |
| 5,415,660 | A | | 5/1995 | Campbell et al. ............... 606/62 |
| 6,127,597 | A | * | 10/2000 | Beyar et al. .................. 606/86 R |
| 6,240,797 | B1 | * | 6/2001 | Morishima et al. ........... 74/89.39 |
| 6,730,087 | B1 | | 5/2004 | Butsch ............................. 606/57 |
| 7,063,706 | B2 | | 6/2006 | Wittenstein ..................... 606/90 |
| 2002/0133225 | A1 | * | 9/2002 | Gordon ........................ 623/1.42 |

(Continued)

FOREIGN PATENT DOCUMENTS

GB    2 333 457    7/1999    ............. A61B 17/72

OTHER PUBLICATIONS

Finland Search Report (2 pages, dated Dec. 2, 2009).

(Continued)

*Primary Examiner* — Mary Hoffman
(74) *Attorney, Agent, or Firm* — Renner, Kenner, Greive, Bobak, Taylor & Weber

(57) ABSTRACT

The invention relates to an internal osteodistraction device, which includes two fixing points (7, 8) for attachment to a bone in such a way that the distance between the fixing points can be increased in a controlled manner, and a magnetostrictive element (1) which produces a reciprocating mechanical motion in a changing magnetic field. The magnetostrictive element is configured for taking up solely a compressive or tensile force, such that the magnetostrictive element pushes a unidirectional movement permitting element which allows for an increase in the distance between the fixing points, and as the magnetostrictive element is in the process of returning to its original length, a second unidirectional movement permitting element allows the magnetostrictive element to resume its original length without changing a distance between the fixing points of the distraction device.

7 Claims, 7 Drawing Sheets

(56) References Cited

U.S. PATENT DOCUMENTS

Figure 1A:
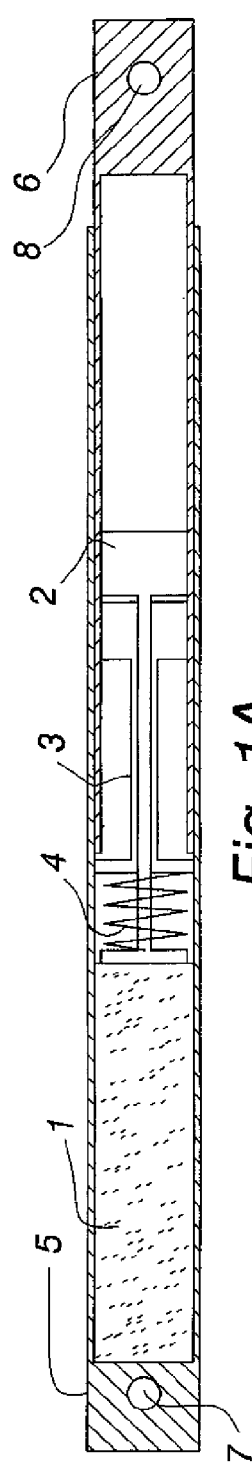

| | | | |
|---|---|---|---|
| 2004/0117024 A1* | 6/2004 | Gerbec et al. | 623/18.11 |
| 2004/0138663 A1* | 7/2004 | Kosashvili et al. | 606/62 |
| 2008/0108995 A1* | 5/2008 | Conway et al. | 606/63 |
| 2009/0062798 A1* | 3/2009 | Conway | 606/63 |
| 2009/0076597 A1 | 3/2009 | Dahlgren et al. | 623/2.1 |
| 2009/0112262 A1* | 4/2009 | Pool et al. | 606/246 |
| 2012/0209269 A1* | 8/2012 | Pool et al. | 606/63 |

OTHER PUBLICATIONS

"A Completely Intramedullary Leg Lengthening Device" (Proceedings of the 20th Annual International Conference of the IEEE Engineering in Medicine and Biology Society; Aalsma, A.M.M., et al.; vol. 20, No. 5, 1998—4 pages).

* cited by examiner

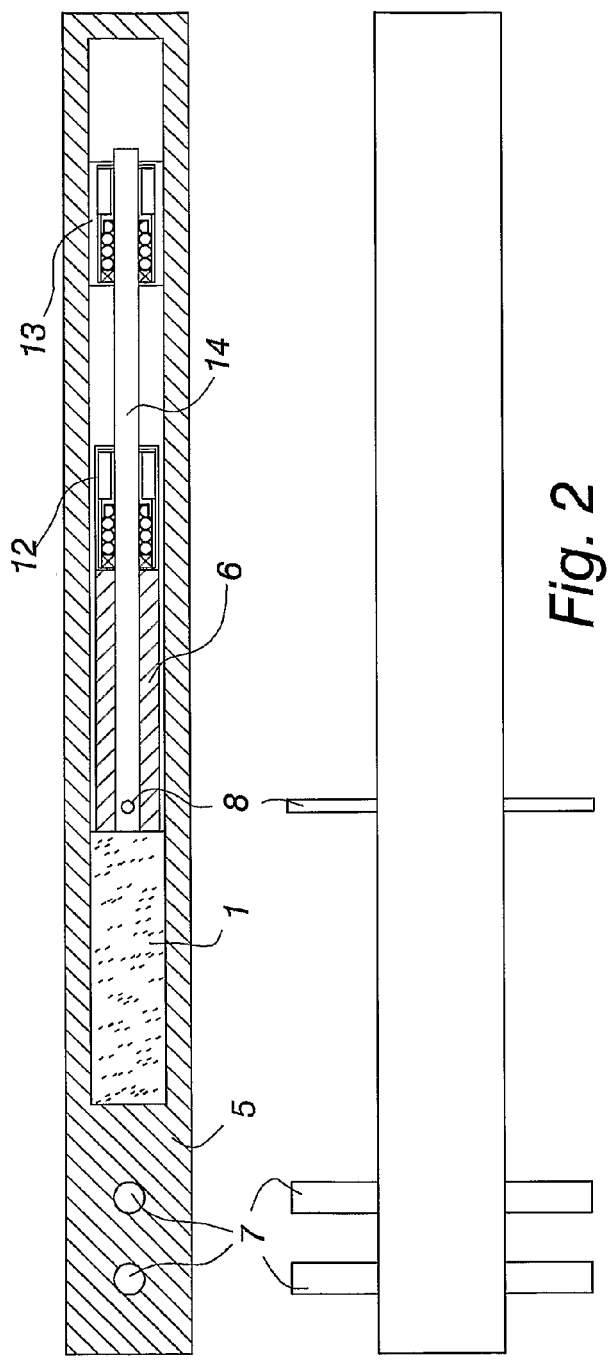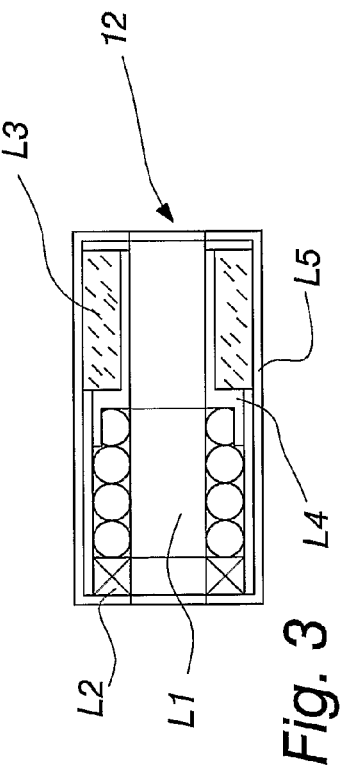

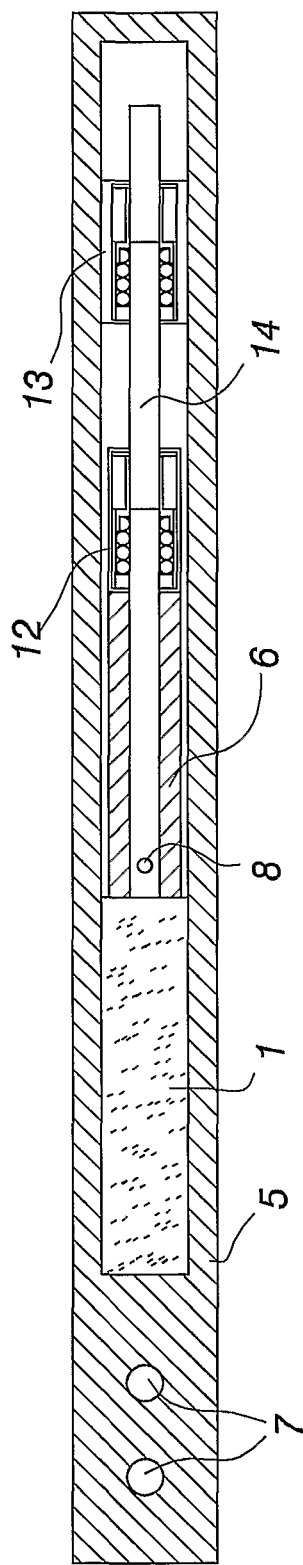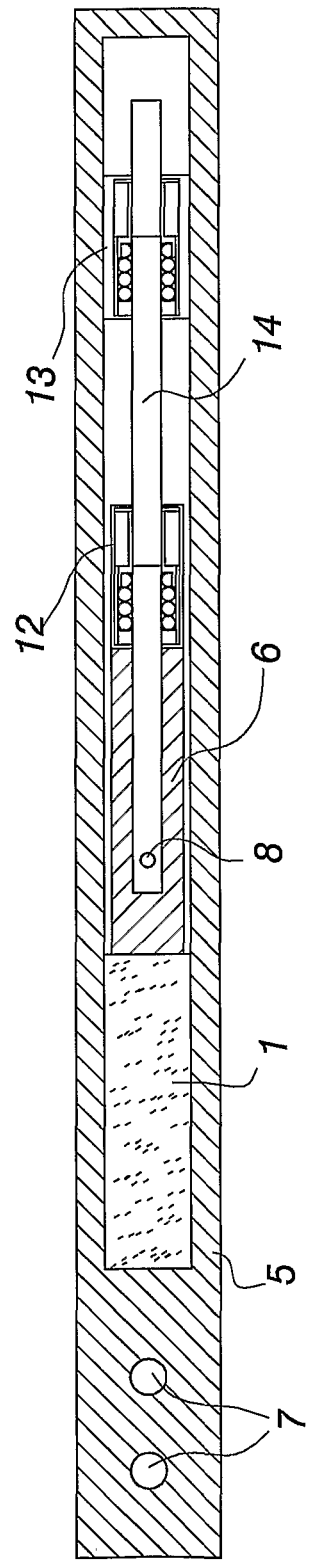
Fig. 4A
Fig. 4B

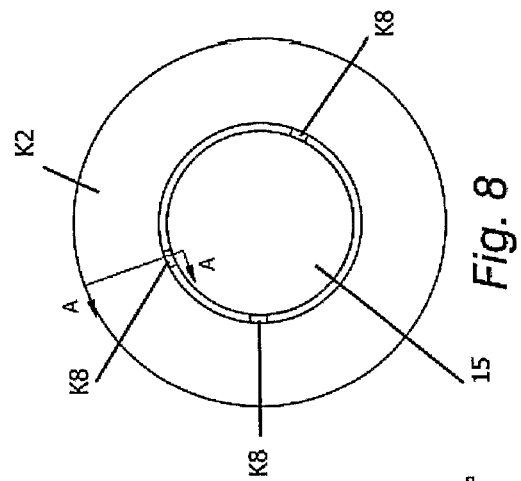
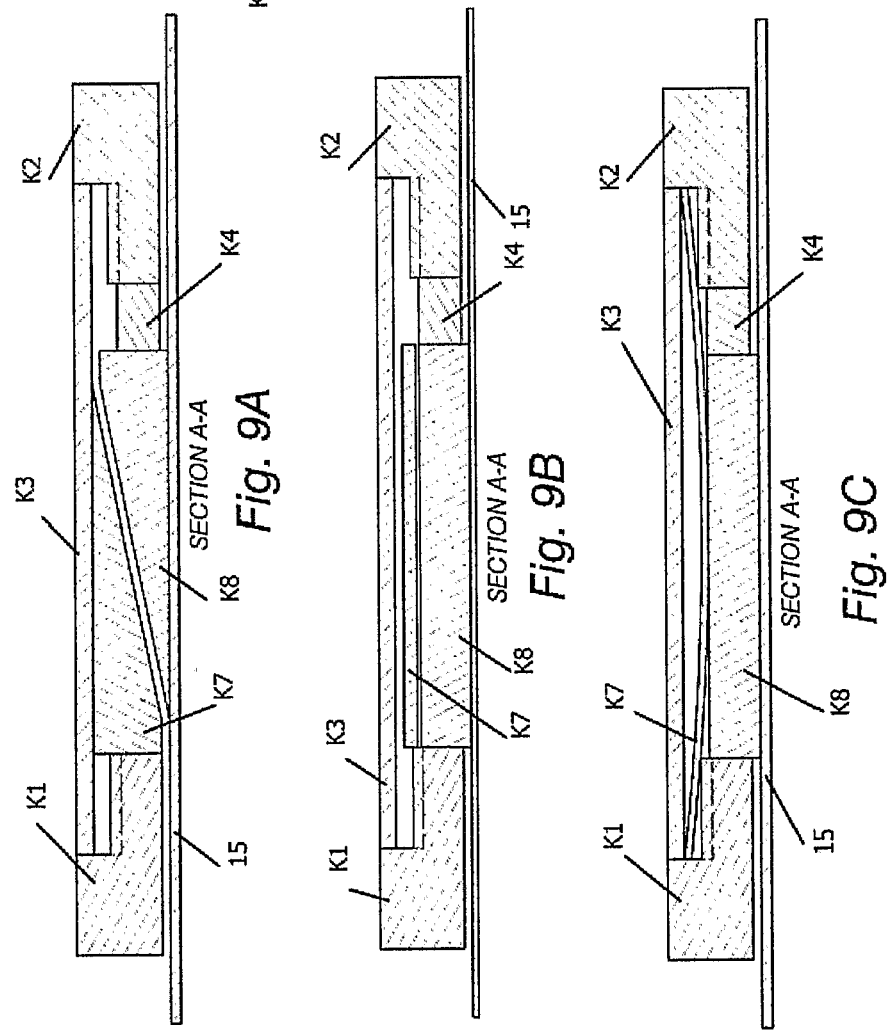

INTERNAL OSTEODISTRACTION DEVICE

TECHNICAL FIELD

The application relates to the details of an intra-corporally installed, patient-friendly distraction-osteogenesis device.

Distraction osteogenesis has emerged since the 1980's as an important remedy in difficult fractures and bone lengthening procedures. In addition, this form of therapy has also gained popularity in the treatment of facial bone defects.

Distraction osteogenesis refers to a method used for lengthening bones and correcting osteostructural defects, such as difficult fractures and deformities. The method is particularly useful in the treatment of long bones, such as the extremities. The method is based on cutting a bone and the bone's ability to form new bone tissue in the fracture site. After the bone has been cut, a distraction device is fitted between the bone segments, and it moves the bone segments away from each other at a daily rate of about one millimeter (1 mm). When about 5-12 days has lapsed from the cutting operation, the formation of new bone tissue begins in the distraction site.

The distraction device must be capable of producing a sufficient amount of force. In the case of extremities, the maximum forces needed for achieving a distraction have been about 1000 Newtons. It is another requirement that the invasive parts of the device, i.e. those in contact with tissue fluid, be biocompatible. Furthermore, the distraction device must remain functionally reliable throughout the entire therapy which lasts about a year.

PRIOR ART

Distraction devices currently in service can be distinctly categorized for extra-corporal and completely intra-corporally implantable models. A drawback in extra-corporal devices is the high risk of infection, the clumsiness and appearance of external devices. In addition, as the bone increases in length, the soft tissues are subjected to stretching and tearing, which causes severe pain and a risk of tissue damage.

Due to a simple design and a reasonably arbitrary choice of materials, the external devices, as a general rule, are considerably less expensive than implantable devices, which is probably the most important reason for their continued use.

Intra-corporally Implantable Devices

Intra-corporally or internally implantable devices enable the elimination of problems inherent to extra-corporal or external devices. The risk of infection, in particular, is significantly reduced. At the moment, implantable devices for the distraction-osteogenesis therapy of legs are only available in two models, neither of which is in worldwide use.

The more widespread of these devices is the Intramedullary Skeletal Kinetic Distractor (ISKD), based on the Albizzia intramedullary rod. Distraction with the ISKD is achieved by rotating the foot over a few degrees, whereby the telescopic intramedullary rod lengthens by virtue of a mechanism included therein. Consequently, the gap between bone segments increases as well. As a result of the lengthening method, the therapeutic process is quite painful for a patient, especially right after the implantation. In the case of active patients, another problem may result from the excessively high-speed progress of distraction because of too much rotating of the foot. Therefore, it is possible that the normal activity of a patient must be restricted during the course of therapy. The result of an excessively high-speed distraction is namely that the formation of new bone tissue is not enough to fill the gap developing between the bone segments and the consequence will be a therapeutic failure, a nonunion. The precision engineering mechanics included in the apparatus is expensive and complicated.

The German-made Fitbone is the only available electrically controlled distraction-osteogenesis device. In this device, the progress of distraction is controlled by an electric motor, the rotation of which is translated by a planetary gear to the lengthening of an intramedullary rod. Power is supplied to the motor by making use of induction between an extra-corporal coil and an intra-corporally implantable secondary coil. However, the device is also available in a version, in which the extra-corporal coil is replaced by an intra-corporally implantable battery as a power source. The device is complicated and expensive.

Along with the foregoing devices, several solutions have been patented which are based on bone marrow nailing, but for some reason those have not emerged in the marketplace. In addition to these, a few novel implantable devices are currently under development.

GB2333457 discloses an osteodistraction device, in which a magnetostrictive element functions as a principal brace element for the device, and elements permitting a unidirectional movement brace themselves against the magnetostrictive element itself. Hence, there is a hazard of the magnetostrictive element breaking as a result of torsion. Moreover, being present at an outer surface of the magnetostrictive element, the unidirectional movement permitting elements increase the device in terms of its total thickness and thus the actual magnetostrictive element remains so small in diameter that a sufficient force cannot be generated thereby.

According to the invention, the magnetostrictive element is configured to have a larger diameter within the device by relocating the unidirectional movement permitting elements forward and/or rearward of the magnetostrictive element. In addition, the magnetostrictive element is set free in a transversal direction, i.e. it only applies a pushing action on the unidirectional movement permitting elements without a possibility of having the magnetostrictive element subjected to torsional or twisting forces. In the case of the above-cited publication GB2333457, the magnetostrictive element may be damaged by torsional or twisting forces applied to an extending limb, whereby the patient is exposed to a serious complication hazard. At the same time, the magnetostrictive element's biocompatible encapsulation breaks up and the bone under extension is exposed to a high risk of nonunion. In addition, a disintegrating mechanical device may always cause serious internal bleeding. Bioencapsulation is difficult to implement, because the encapsulation should allow for strains of a magnetostrictive material and the material should take up the forces produced by barbs which permit a unidirectional movement.

It is an objective of the invention to provide an implantable distraction-osteogenesis device, which is controlled wirelessly from outside the body and which is more economical than before to manufacture and use, as well as reliable in operation and simple and economical to manufacture and modify according to a patient.

Operating Principle

The device is an intra-corporally implantable intramedullary rod, which is controlled by means of a magnetic field from outside the body. The change of length is achieved by exploiting the ability of a magnetostrictive material, e.g. such as sold under the trade name Terfenol-D, to change its length in an external magnetic field (Joule magnetostriction). The device has its drive mechanism implemented on a step motor principle. Thus, a short one-step elongation of the magnetostrictive material can be translated into a total elongation sufficient for distraction. The device is controlled by means of short magnetic pulses generated by an extra-corporal coil, eliminating completely the need for intra-corporal electronics. The material, which is sold under the name Terfenol-D, has a formula $Tb_xDy_{(1-x)}Fe_y$, wherein X is about 0.3 and Y is about 1. In this application, the material is referred to by the generally known trade name, but it can be replaced by any equivalent material referred to by the term Giant Magnetostrictive Material. Terfenol-D offers the benefit of a large-scale magnetostrictive movement, but there are other commonly known equivalent materials which are useful in this application.

BRIEF PRESENTATION OF THE DRAWINGS AND DESCRIPTION OF THE INVENTION

Figure 1B:
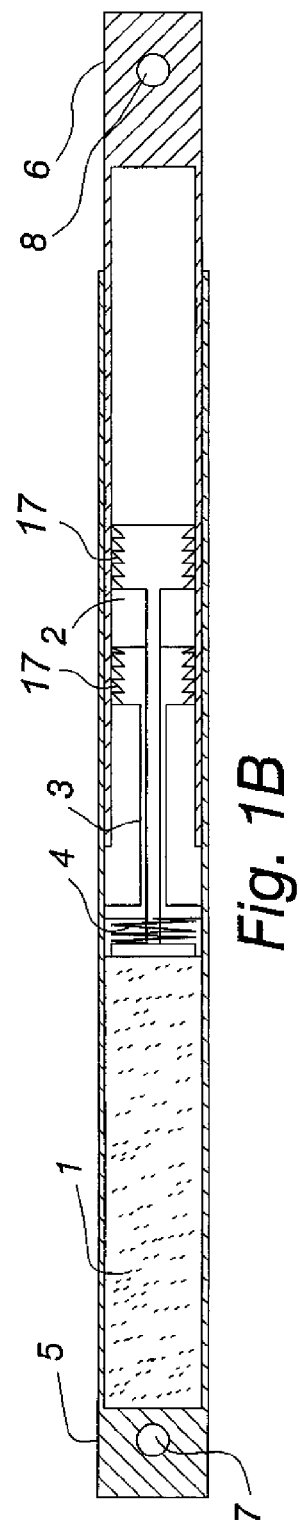
Figure 1C:
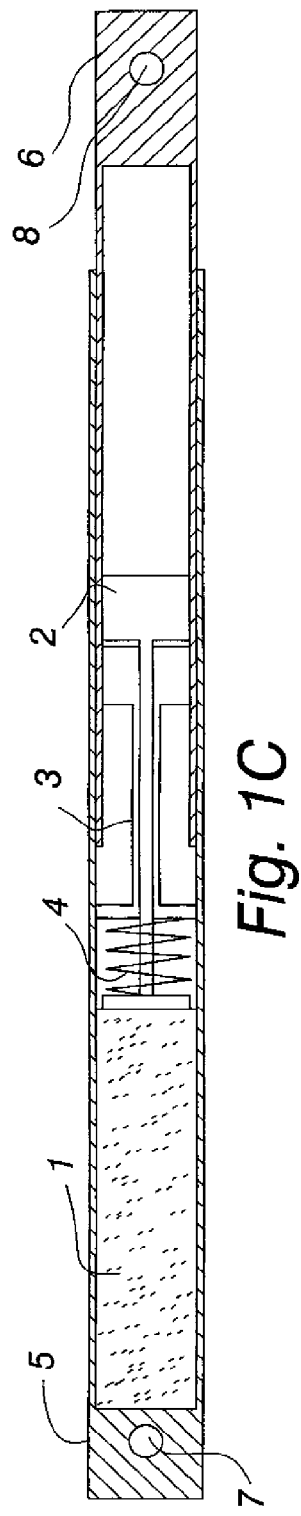
Figure 4C:
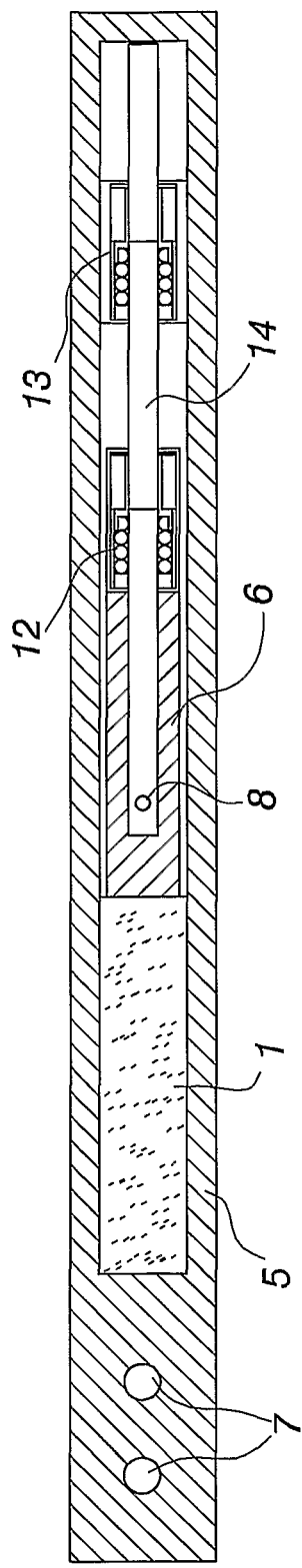
Figure 4D:
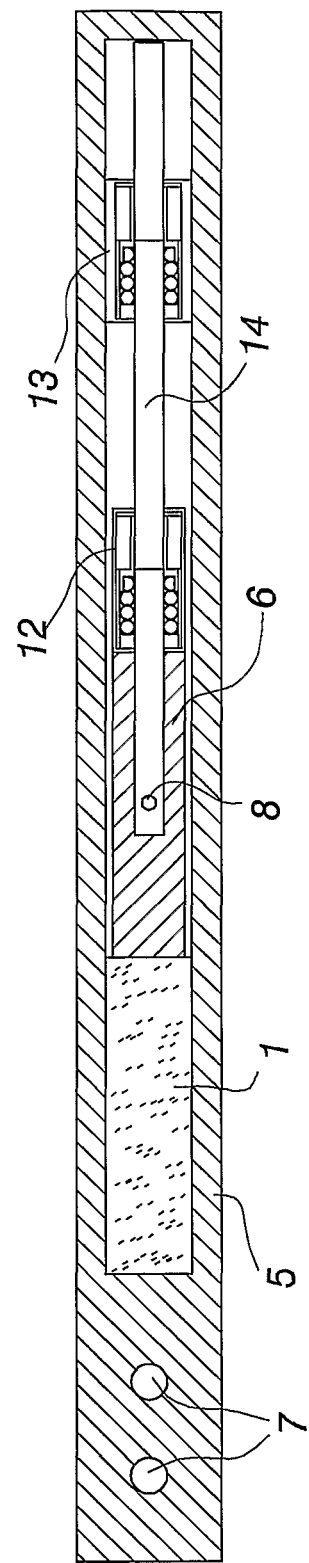
Figure 5:
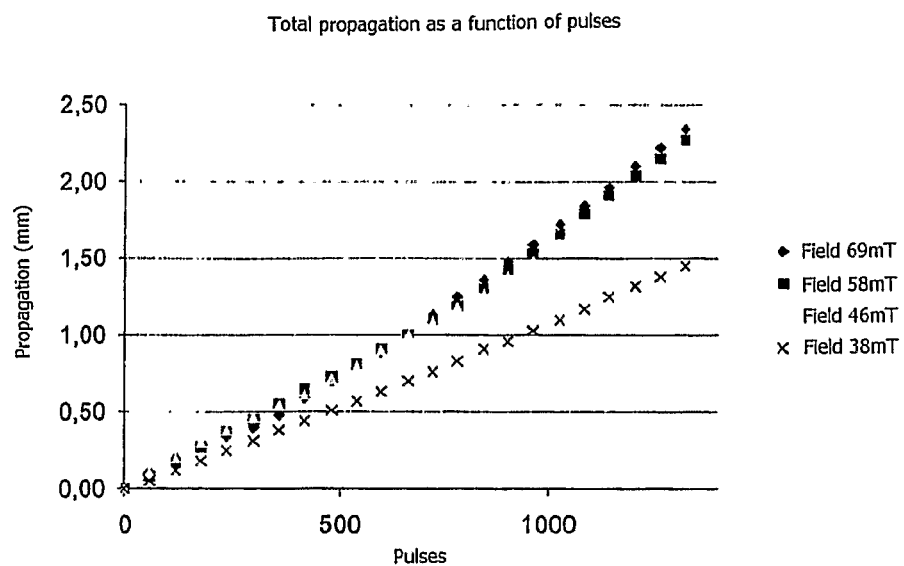
Figure 6:
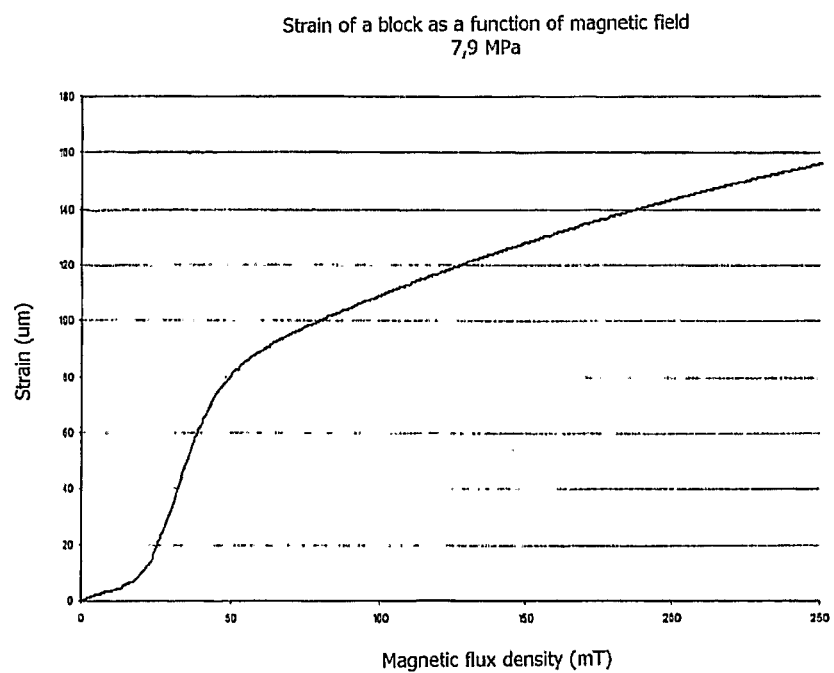
Figure 7:
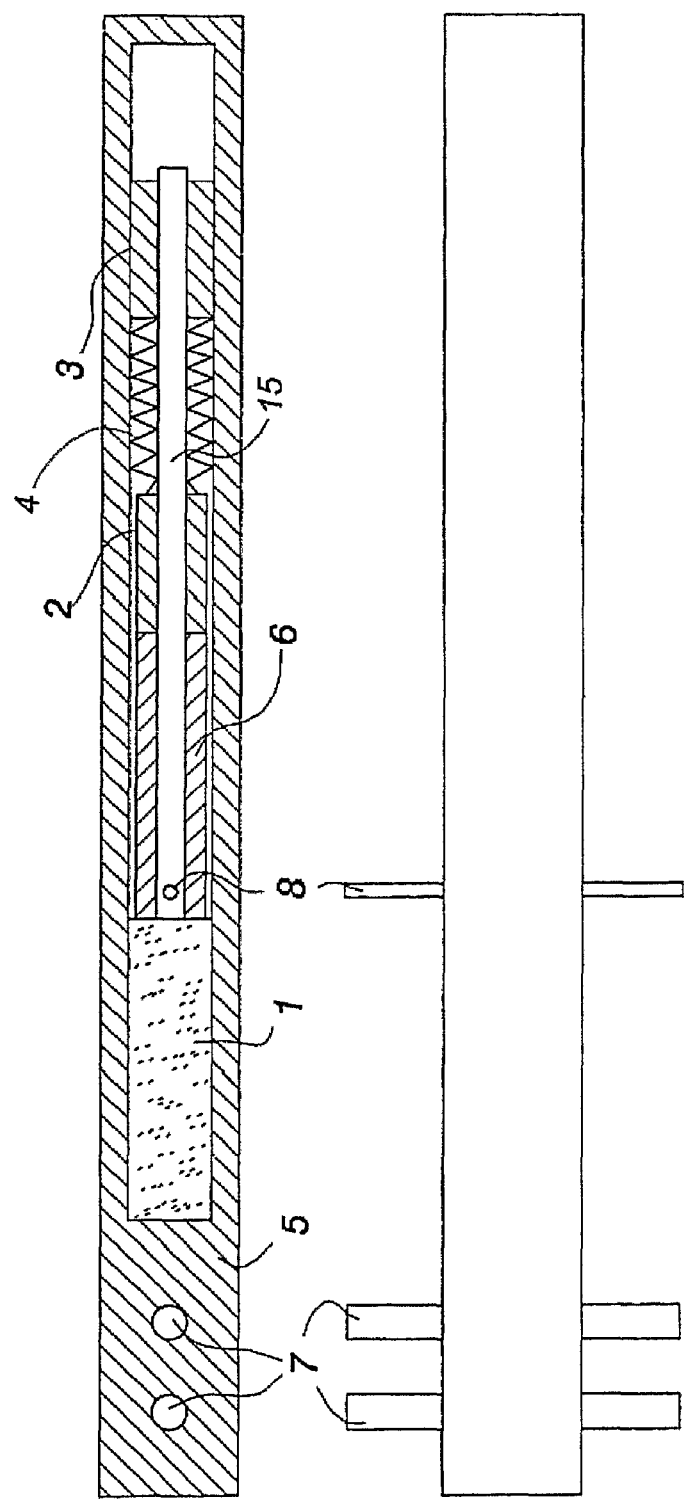

FIGS. 1A-1C illustrate a device according to a first embodiment in various phases of its sequential operation, FIG. 2 shows a device according to a second embodiment in a view of principle, FIG. 3 shows a detail of the preceding device, FIGS. 4A-4D show a device according to the second embodiment in its sequential operation during its extension, FIG. 5 shows a total extension for a prototype device as a function of the number of pulses, FIG. 6 shows an elongation for the magnetostrictive element of a prototype device as a function of the magnetic field, FIG. 7 shows a device according to the first embodiment in a variation, FIG. 8 shows a unidirectional movement permitting element in an axially directed view, and FIGS. 9A-9C show unidirectional movement permitting elements in axially directed cross-sections.

FIG. 1 shows an intra-bone device, including an outer tube 5 provided with a bone fixing point 7, and an inner tube 6 which is attached to the bone at a fixing point 8. The apparatus is simple to such an extent that the components can be changed prior to surgically inserting the device inside the body, thus enabling the device to be varied in terms of its length and maximum elongation. The device components can even be reduced in length at a later stage. This enables an adaptation of the device to each patient while still in the treating hospital. The fixing points are not illustrated in detail; the fixing points 7 and 8 are connected to actual bone fixation means.

The device lengthening force is generated by an element 1, which is magnetostrictive or made of a magnetic shape memory material, preferably e.g. Terfenol-D. The magnetostrictive element 1 is depicted in FIG. 1 in a condition of the magnetic field not producing a lengthening force. In FIG. 1B, the element 1 has increased in length and is in the process of pushing a member 2 ahead of itself. Since the member 2 has its inner-tube contacting surface provided with unidirectional movement permitting elements 17, the member 2 is pushing the inner tube ahead of itself. In FIG. 1C, the magnetostrictive element 1 resumes its initial position after the magnetic field has become deactivated. Now, a member 3 retains the inner tube from returning back and a spring 4 is in the process of compressing the magnetostrictive element and at the same time pulling the member 2 back for another operating cycle.

According to one embodiment of the device, the spring 4 can be replaced with an element made of a superelastic material, for example with a wire or a thin rod, which is adapted to extend through or around the element 1. An appropriate superelastic material is NiTi, nickel titanium. It is sold under the trade name Nitinol and is available in different variations for different temperature ranges and various uses. In this particular intended use, the temperature is highly constant and the choice of a suitable material is not difficult. Hence, the spring 4 can be replaced with a compact device, producing a springback factor which remains almost constant throughout the working cycle. In addition, NiTi is a highly durable and stable material, which is used in also medicine even at the moment.

The unidirectional movement permitting elements can be for example barbs of spring steel, which bite into the inner tube's surface and permit a movement in one direction only. The unidirectional movement permitting elements can also be provided in a configuration other than the one described here. For example, there may be another element at the inner tube's outer surface for a direct influence on the outer tube. In this case, the springs themselves can also be housed in the inner tube. In addition; the NiTi material can also be used for controlling the unidirectional movement producing elements. Thus, the device can have its initial length adjusted by warming up the shape memory alloy sufficiently through heating the entire device and, after the device has cooled down, the unidirectional movement permitting elements start working again. It is also possible to conduct the warming-up process during the course of implantation surgery by heating the elements locally, for example inductively or by means of an appropriate tool. In addition, the action can be promoted by conditioning the tube's inner surface, for example by fluting or roughening. Regarding heat-activated shape memory alloys, e.g. NiTi is biocompatible, i.e. its use as a spring element is preferred. In addition, the elements can be simply released by heating for easier assembly, cleaning and installation. With the device inside the body, the shape memory alloy preferably functions in a superelastic state, i.e. it is not controlled by means of heat during its operation.

FIG. 7 shows a variation for a device according to the first embodiment. The device consists of components as follows: a magnetostrictive element 1, an outer tube 5, an inner tube 6, bone fixators 7 and 8, two unidirectional movement permitting elements 2, 3, a rod 15, and a spring 4. As the magnetostrictive element 1 increases in length, the inner tube 6 transmits a pushing motion to the unidirectional movement permitting element 2. This is positioned for pushing the rod 15 to the right, where the other movement permitting element 3 is attached to the outer tube 5 and positioned so as to allow the rod 15 to pass through the movement permitting element 3. As the magnetostrictive element 1 becomes shorter, the spring 4 returns the unidirectional movement permitting element 2 and the inner tube 6 to the original position without the rod 15, and thereby the right-hand side fixing point 8, returning to the initial point. The spring 4 produces a bias in the magnetostrictive element 1. The unidirectional movement permitting element 3 is positioned for preventing the rod 15 from moving to the left in the figure.

An axially directed view of the unidirectional movement permitting elements 2 and 3 is depicted in FIG. 8, consisting of components as follows: a clamping block K8, an end piece K2, and a rod 15. There may be several clamping blocks K8 along the circumference. FIGS. 9A-C illustrate sections A-A in FIG. 8. The unidirectional movement permitting elements 9A-C consist of components as follows: an end plug K1, K2, a shell K3, a spring K4, a rod 15, a compression block K7, and a clamping block K8. As the rod 15 pushes to the right, the compression block K7 yields upward in the figure, allowing for a movement of the rod 15 to the right. The spring K4 returns the clamping block K8 to the left, locking the rod in a new position and eliminating a locking gap. The compression block K7 can be configured e.g. as a wedge-like member 9A-K7, as a collar 9B-K7 compressing simultaneously all the clamping blocks around the same, or as a spring 9C-K7 compressing the clamping block. An engagement of the clamping block K8 with the rod 15 can be implemented by exploiting the compression or by conditioning respective surfaces of the rod 15 and the clamping block K8 for permitting a unidirectional movement only.

Typically, the femur traction device effects a one-step magnetostrictive displacement in the order of 100 μm, whereby a gap in the order of about 30-70 μm can be accepted in a unidirectional movement permitting element. Thus, the pattern of for example 30 μm is convenient in the components of an osteodistraction device.

FIG. 2 depicts a model according to a second embodiment. This second possible way of implementing a step motor comprises the application of available bearing mechanisms in a presumably whole new manner. In this case, the step motor consists of components as follows: a ball screw 14, two ball screw nuts, as well as two one-way clutches 12, 13. The one-way clutches L3 include two components, outer and inner covers. The operation of these two is such that, as the inner cover is rotated in one direction, the outer cover does not rotate with it. Respectively, when rotating in the other direction, the outer cover is also co-rotating, i.e. the bearing is now transmitting a torque. As Terfenol-D stretches further, a bearing mechanism 12, shown on the left-hand side in the figure, works its way slightly to the right. Thus, the ball screw moves to the right as well, because the left-hand side mechanism 12 has its one-way clutch set in such a way that the nut is disabled from rotating around the ball screw while the pushing action continues. At the same time, in a right-hand side bearing mechanism 13, the ball screw 14 has its nut L1 rotating, because the one-way clutch L3 included therein is set in a reverse manner with respect to the former. Respectively, when the magnetostrictive element 1 becomes shorter, the ball screw of the left-hand side mechanism 12 has its nut L1 rotating, and the one-way clutch L3, which bars rotation of the nut in the right-hand side mechanism 13, precludes a retraction of the ball screw together with Terfenol back to the left. L2 is a bearing which takes up lengthwise forces and permits rotation. The ball screw 14 itself does not rotate in this example, but it only functions as a pushing element, and the ball nuts function as unidirectional movement permitting elements. In this application, the inner tube 6 lies completely inside the outer tube 5, and the fixation to bone takes place by means of a fixator 8 through a slot in the outer tube to the ball nut. The inner tube 6 functions as a pushing element. Preferably, the bone engaging element can be a more extensive element supported on the outer tube, and the inner tube function, described herein, can be replaced by a channel attached to a bearing of the element 12. In case the fixator 8 is in the illustrated position inside the inner tube, it is necessary that the inner tube 6, or the channel serving as its replacement, and the outer tube 5 be both provided with a groove which permits a movement of the fixator 8.

FIGS. 4A-4C present the lengthening cycles in a device according to the second embodiment. In FIG. 4A, the magnetostrictive element is in a lengthened condition and the inner tube is compressing a ball nut assembly 12. Because the mechanism 12 does not allow rotation, the ball nut moves and locks in its new position. The movement is allowed by a mechanism 13.

In FIG. 4B, the ball nut mechanism 12 allows a movement and the inner tube 6 returns back. At this time, the ball nut mechanism 13 does not allow a movement and the ball screw remains stationary.

Likewise, FIG. 4C shows a repetition of what happens in FIG. 4A, and FIG. 4D shows a repetition of what happens in FIG. 4B, and the ball screw advances across the next cycle.

Due to mechanical tolerances, the post-pushing length of the device is set back slightly as the length of the magnetostrictive material retracts, i.e. the elements blocking a returning movement are not ideally functional, but always exhibit a small play. Because the magnetostrictive displacement is small, this return displacement can be several tens of percent of the pushing motion distance. This is not harmful to bone distraction, as long as the extent of a pushing cycle exceeds that of a return cycle. It has also been discovered that this type of oscillation and a repeated change of the bone length in fact accelerates the bone growth and results in a stronger bone. This is why a controlled play is even preferred from the standpoint of recuperation, as long as a desired net elongation or lengthening rate is achieved. If it is desirable to intentionally produce small movement in an osteosynthetic site, the device can be provided with a small clearance or flexion and the generation of a reciprocating motion is effected by using a low-intensity magnetic field, whereby the unidirectional movement permitting elements do not produce a significant elongation.

In order to effect the play-induced return motion and the total elongation in a controlled fashion, it is either necessary to know the extent of advancing and returning movements, such that the net movement produced by each magnetic pulse is known, or the device can be fitted with a change-of-length measuring instrument. The measuring instrument can be provided with a communication link, using radio waves, a magnetic field, or ultrasound for its operation. It may function in a mode measuring a proportional change in length, i.e. it may be based for example on the 3-bit scale of a measuring sensor for an identical measuring result at the intervals of 8 steps. The number of bits can naturally be higher or lower. Thus, even a reciprocating motion does not hinder the calculation of a length displacement, as long as the calculator reading does not change too many measuring steps at a time so as to exceed a cycle length of the measuring sensor. The calculator can have its measuring element in association with a ball nut or with a reset motion precluding, unidirectional movement permitting element. In practice, for example, a one-time movement is 100 μm at its maximum and is followed by a return movement of e.g. 10-60 μm, whereby the total displacement must lend itself to be measured at a resolution of about 100 μm, which means that 50-100 μm is sufficient for a step in the measuring scale, whereby the one-step displacement shall never be close to the total cycle length of the scale.

The measurement by a sensor can be based, for example, on mechanical switches, optical, acoustic or capacitive or magnetic elements. A magnetic sensor is able to measure a change in the direction of a magnetic field for example by means of two coils, whereby the coils' phase difference can be used for working out the rotational phase of a ball nut. A magnetic field capable of expanding Terfenol is co-directional with the movement, thus requiring a second magnetic field transverse thereto for measurement or, alternatively, the field controlling elements are used for creating densifications which direct the field to Hall sensors or to coils with the effect that the rotational motion of the ball nut changes a flux proceeding through the sensor coils. It is also possible to use a measuring wheel, which is driven by a linear motion, such that the direction of coils included in the wheel relative to a magnetic field changes with respect to a longitudinal magnetic field. In this case, the transmission ratio must be of such a magnitude that the movement of about 1 mm spins the measuring wheel sufficiently for measuring the phase difference reliably.

The respectively lengthwise moving sensor coils or Hall sensors are able to detect gaps, ridges or grooves in a magnetic material present on a moving element. Infrared radiation can also be used intra-corporally in a measuring sensor as IR transmits sufficiently well through bodily fluids.

In the event that a mechanical sensor is employed, said sensor need not follow the reset motion at all but, for example, the sensor can be completely disengaged from its pushing element for the duration of a return movement.

Consequently, the possible reciprocating motion does not interfere with a measuring process, nor does the measuring instrument become worn as a result of the reciprocating motion.

Both embodiments of an osteodistraction device enable the elimination of problems associated with extra-corporal or external devices, such as a high risk of infection, as well as psychological and social downsides. The use of a magnetostrictive and superelastic material for establishing a movement as described above enables providing a functionally reliable, simple and trustworthy apparatus. Furthermore, as a result of its simplicity the apparatus readily lends itself to the replacement and variation of its components, making it easier than before to provide the apparatus with a length that is appropriate for different patients.

In addition, the progress of distraction lends itself to a precise control as the preliminary prototype developed in our laboratory enables a progression of a few millimeters at a time. A slow lengthening rate can ease the stress conditions created in tissues and promote thereby a speedy physical recovery from the treatment.

Moreover, the device is structurally quite simple, enabling a high functional security and reliability. In another aspect, the simple structure probably enables a low price for the device, which might make a major difference for a potential success of the device in the marketplace while making a patient-friendly form of distraction osteogenesis therapy available for as many people as possible.

Other Application Fields For The Invention

Miniaturization of the device enables also a facial distraction-osteogenesis therapy. In miniaturization, the magnetostrictive Terfenol-D is replaced for example by a magnetic shape memory alloy, which enables more extensive one-step elongations. Terfenol-D can be replaced as the distraction treatment of a facial area does not require forces of the same magnitude as those needed in the context of extremities.

A device according to the invention can also be used in the treatment of scoliosis. In this case, the brace element is lengthened as the child patient is growing. This makes it possible that, during the course of an on-going therapy, the length of an intra-corporal brace used in the treatment of scoliosis be changed. Hence, as the child patient is growing, the brace can be increased in size without renewed surgery. The treatment of scoliosis can be performed with forces less powerful than those needed in bone lengthening therapy. On the other hand, there may be a plurality of necessary brace points, whereby force must be distributed among several brace points for example by means of a spring or several ball nut assemblies. Alternatively, there are several unidirectional movement permitting elements in succession, whereby one or more strain-producing elements create a reciprocating movement for several fixing points. Thus, the reciprocating movement permitting elements may function in such a way that the distance between two successive brace points changes on every push with respect to the adjacent brace point or each gap between brace points has a separate independent mechanism with its motion producing elements.

Another possibility is to employ a superelastic outer shell, having brace points disposed in such a manner that the shell is stretched with a single common mechanism. In this case, it is even possible to configure the entire device as a hermetically sealed rod, whereby the outer shell consists, for example, of nickel titanium which is superelastic at body temperature.

The device's motor unit may find applications also in other fields of health technology, for example in medical dispensers, in which it could function as a drive component for various pumps and valves. A high-precision linear motor may find applications also in other technical fields. Furthermore, a combination, involving a superelastic heat-sensitive shape memory alloy and a magnetic shape memory alloy or a magnetostrictive alloy, is useful as a linear motor in many other applications as well, in which a unidirectional movement is required. In the capacity of a returning element, a superelastic shape memory alloy is preferred because of its properties, and a shape memory alloy, used in unidirectional movement producing elements, allows, by heating the device or the elements, a return movement of the device to its original condition or a disassembly of the device for cleaning, for example.

Demonstration Results

FIGS. 5 and 6 illustrate the inventive idea in terms of its functionality. The trial involved testing the motor unit for its operation in a pulsed external magnetic field of varying magnitude. The data in FIG. 5 shows a total change in the length of a distraction device, i.e. the propagation as a function of pulses generated by an external magnetic field. This indicates that the one-millimeter daily elongation, required for distraction therapy, is accomplished in 5-6 minutes when the pulses have a frequency of 2 Hz. The length of a single step in the field of 69 mT is 1.8 µm and it can be influenced by changing the external magnetic field.

FIG. 6 shows the elongation of a magnetostrictive material, used for the motor unit of a distraction device, as a function of an external magnetic field in the trial condition of FIG. 1. It can be seen in FIG. 6 that the length of a single step can be influenced by changing the external magnetic field, especially in coincidence with a steep climb of the graph. This is supported by the measurements of FIG. 5, of which the elongations caused by three highest magnetic fields are almost identical. These flux densities of a magnetic field coincide with a latter bend present in the graph of FIG. 6.

The invention claimed is:

1. An internal osteodistraction device, including two fixing points (7, 8) for attachment to a bone in a way that enables increasing the distance between the fixing points in a controlled manner, a magnetostrictive element (1) capable of producing a reciprocating mechanical motion in a changing magnetic field, and unidirectional movement permitting elements, wherein when the magnetostrictive element is only subjected to compressive or tensile forces, the magnetostrictive element is adapted to push a member (2), where said member engages said unidirectional movement permitting elements, allowing for increasing a distance between the fixing points, and as the magnetostrictive element is in process of returning to its original length, a second member (3) engages said unidirectional movement permitting elements and allows the magnetostrictive element to resume its original length in such a way that the distance between the fixing points of the distraction device does not change substantially or that the distance between the fixing points retracts to a lesser extent than what was the increase of the distance therebetween as a result of the pushing action, wherein the magnetostrictive element acts on the members that engage the unidirectional movement permitting elements, and the members and unidirectional movement permitting elements are located only between the magnetostrictive element and one of the two fixing points.

2. An internal osteodistraction device as set forth in claim 1, wherein the magnetostrictive element is influenced by a superelastic element, which produces in the magnetostrictive element (1) a retraction force and/or a bias.

3. An internal osteodistraction device as set forth in claim 1, wherein the unidirectional movement permitting elements include a shape memory alloy element.

4. An internal osteodistraction device as set forth in claim 1, wherein the length of the device and maximum strain length of the device are adjustable by cutting or by selecting appropriate components.

5. An internal osteodistraction device as set forth in claim 1, wherein the unidirectional movement permitting elements comprise barbs or ratchet members.

6. An internal osteodistraction device as set forth in claim 1, wherein the unidirectional movement permitting elements comprise a ball nut and a one-way clutch.

7. An internal osteodistraction device as set forth in claim 1, wherein the device comprises elements measuring a change of length.

* * * * *